United States Patent [19]

Breuer et al.

[11] 3,962,229
[45] June 8, 1976

[54] 2-(THIOCARBONYLAMINO)ACETAMIDO-7α-METHOXY CEPHALOSPORANIC ACID COMPOUNDS

[75] Inventors: Hermann Breuer; Uwe D. Treuner, both of Regensburg, Germany

[73] Assignee: E. R. Squibb & Sons, Inc., Princeton, N.J.

[22] Filed: May 28, 1975

[21] Appl. No.: 581,449

[52] U.S. Cl. .............................. 260/243 C; 424/246
[51] Int. Cl.² ........................................ C07D 501/20
[58] Field of Search .................................. 260/243 C

[56] References Cited
UNITED STATES PATENTS

| | | | |
|---|---|---|---|
| 3,819,621 | 6/1974 | Morimoto et al. | 260/243 C |
| 3,855,211 | 12/1974 | Breuer et al. | 260/243 C |

*Primary Examiner*—Nicholas S. Rizzo
*Attorney, Agent, or Firm*—Lawrence S. Levinson; Merle J. Smith

[57] ABSTRACT

New 2-(thiocarbonylamino)acetamido-7α-methoxy cephalosporanic acid compounds of the following general formula, and their salts,

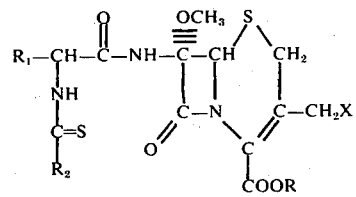

wherein R is hydrogen, lower alkyl, phenyl-lower alkyl, tri(halo)lower alkyl, a salt forming ion or the group

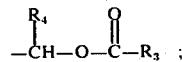

$R_1$ is hydrogen, lower alkyl, cyclo-lower alkyl, unsaturated cyclo-lower alkyl, phenyl, substituted phenyl, furyl, thienyl or pyridyl; $R_2$ and $R_4$ each is hydrogen or lower alkyl; $R_3$ is lower alkyl, phenyl or phenyl-lower alkyl; and X is hydrogen, lower alkanoyloxy or azido; are useful as antibacterial agents.

11 Claims, No Drawings

2-(THIOCARBONYLAMINO)ACETAMIDO-7α-METHOXY CEPHALOSPORANIC ACID COMPOUNDS

SUMMARY OF THE INVENTION

This invention relates to new antibacterial α-thiocarbonylamino-7α-methoxycephalosporanic acid compounds of the formula

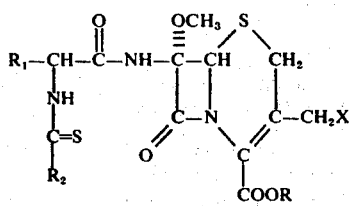

R represents hydrogen, lower alkyl, phenyl-lower alkyl, a salt forming ion or the group

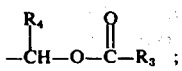

$R_1$ represents hydrogen, lower alkyl, cyclo-lower alkyl, unsaturated cyclo-lower alkyl, phenyl, substituted phenyl wherein the phenyl substituents are lower alkyl, halogen, hydroxy, amino, ureido or methylsulfonylamino, furyl, thienyl or pyridyl; $R_2$ and $R_4$ each represents hydrogen or lower alkyl; $R_3$ represents lower alkyl, phenyl or phenyl-lower alkyl; and X is hydrogen, lower alkanoyloxy or azido.

Especially preferred members within each group are as follows: R is hydrogen, lower alkyl or alkali metal, especially hydrogen, methyl, sodium or potassium; $R_1$ is hydrogen, phenyl or thienyl, especially the latter two; $R_2$ is hydrogen or lower alkyl, especially methyl; $R_3$ is lower alkyl, preferably methyl or t-butyl; and $R_4$ is hydrogen.

DETAILED DESCRIPTION OF THE INVENTION

The various groups represented by the symbols have the meanings defined below and these definitions are retained throughout this specification.

The lower alkyl groups are straight or branched chain hydrocarbon radicals having one to seven carbons in the chain, for example, methyl, ethyl, propyl, isopropyl, butyl, isobutyl, t-butyl, amyl or the like. The $C_1$ to $C_4$ alkyl groups are preferred. The lower alkenyl groups are monounsaturated hydrocarbon radicals of the same type, the two to four carbon members being preferred.

The cycloalkyl groups include cycloaliphatic groups having four to seven carbons in the ring such as cyclobutyl, cyclopentyl, cyclohexyl and cycloheptyl as well as these cyclic groups with one or two double bonds, e.g., cycloalkenyl and cycloalkadienyl groups like cyclobutenyl, cyclopentenyl, cyclohexenyl, cyclopentadienyl, cyclohexadienyl, etc. The double bond or bonds may be variously located. The $C_5$ and $C_6$ cycloalkyls are preferred and particularly preferred is the 1,4-cyclohexadienyl group.

The phenyl-lower alkyl groups are those having a phenyl attached to a lower alkyl group like those defined above, e.g., benzyl (which is preferred), phenethyl and the like, as well as those having two phenyl groups like benzhydryl (another preferred group).

The lower alkanoyloxy groups include the acyl group of acid esters, e.g., acyl radicals of lower fatty acids, for example, acetoxy, propionyloxy, butyryloxy and the like. The heterocyclic groups can be 2-thienyl, 3-thienyl, 2-pyridyl or 3-pyridyl.

The halogens are the four common halogens with chlorine and bromine being preferred.

The salt forming ions are metal ions, e.g., aluminum, alkali metal ions such as sodium or potassium, alkaline earth metal ions such as calcium or magnesium, or amine salt ions, like dibenzylamine, lower alkylamines, e.g., methylamine, triethylamine, etc.

The compounds of formula I are produced by reacting a compound of the formula

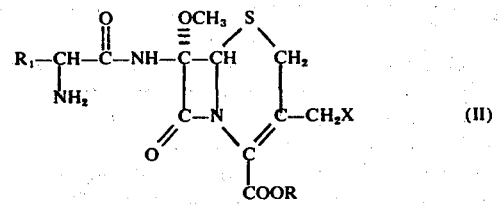

with a compound of the formula

wherein Y is an activating group like lower alkoxy, halogen, —S—CH$_2$—COOH or the like, in a medium like methylene chloride in the presence of a base like triethylamine.

Alternatively, a compound of the formula

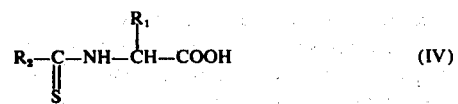

or an activated derivative thereof, like a mixed anhydride or activated ester is made to react with a 7-amino-7α-methoxycephalosporanic acid compound of the formula

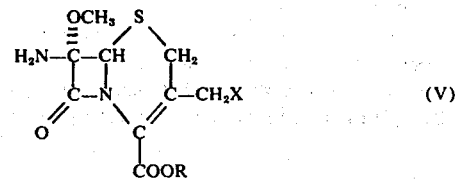

in a medium such as methylene chloride or tetrahydrofuran. A coupling agent like dicyclohexylcarbodiimide can also be used to advantage.

When R is the acyloxymethyl group

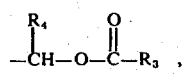

this group may be introduced onto the 7-amino-7α-methoxycephalosporanic acid moiety either prior to or subsequent to the reaction with the compound of formula III or formula IV by treatment with one to two moles of a halomethyl ester of the formula

wherein hal is halogen, preferably chlorine or bromine, in an inert organic solvent such as dimethylformamide, acetone, dioxane, benzene or the like at about ambient temperature or below.

The products of this invention form basic salts with the acid group which are also part of the invention.

It will be appreciated that certain of the compounds of this invention exist in various states of solvation as well as in different isomeric or optically active forms. The various forms as well as their mixtures are within the scope of this invention.

Ordinarily the new compounds of this invention having the D-form are more active than the corresponding compounds having the L-form or DL-form.

Further process details are provided in the illustrative examples and, in addition to showing preferred embodiments, they also serve as models for the synthesis of other compounds of the invention. Starting materials of formula II and V are produced as described in British Pat. Nos. 1,348,984 and 1,348,987, Mar. 27, 1974, and Belgian Pat. No. 768,528, Dec. 15, 1971.

The compounds of this invention have a broad spectrum of antibacterial activity against both gram positive and gram negative organisms such as *Staphylococcus aureus*, *Salmonella schottmuelleri*, *Pseudomonas aeruginosa*, *Proteus vulgaris*, *Escherichia coli* and *Streptococcus pyogenes*. They may be used as antibacterial agents to combat infections due to organisms such as those named above, and in general may be utilized in a manner similar to cephradine and other cephalosporins. For example, a compoound of formula I or a physiologically acceptable salt thereof may be used in various animal species in an amount of about 1 to 200 mg/kg, daily, orally or parenterally, in single or two to four divided doses to treat infections of bacterial origin, e.g., 5.0 mg/kg is effective in mice.

Up to about 600 mg. of a compound of formula I or a physiologically acceptable salt thereof may be incorporated in an oral dosage form such as tablets, capsules or elixirs or in an injectable form in a sterile aqueous vehicle prepared according to conventional pharmaceutical practice.

The following examples are illustrative of the invention. All temperatures are in degrees celsius. Additional variations may be produced in the same manner by appropriate substitution in the starting material.

EXAMPLE 1

7α-Methoxy-3-methyl-8-oxo-7β-[D-2-phenyl-2-(thioformamido)acetamido]-5-thia-1-azabicyclo[4.2.-0]oct-2-ene-2-carboxylic acid and potassium salt 3.78 g. (0.01 mol.) of 7-(D-2-amino-2-phenylacetamido)-7α-methoxy-3-methyl-8-oxo-5-thia-1-azabicyclo[4.2.0]oct-2-ene-2-carboxylic acid are suspended in 50 ml. of methylene chloride and brought into solution with 1.38 ml. (0.01 mol.) of triethylamine. 0.9 g. (0.01 mol.) of ethylthioformate are added and the solution is stirred overnight at room temperature. This is then treated with activated carbon, filtered and stirred with 500 ml. of ether. The precipitate is filtered under suction, dissolved in a little water and acidified to pH2 with dilute hydrochloric acid to 7α-methoxy-3-methyl-8-oxo-7β-[D-2-phenyl-2-(thioformamido)acetamido]-5-thia-1-azabicyclo[4.2.0]oct-2-ene-2-carboxylic acid. This product is dissolved in a little methanol, a 2 N solution of potassium ethylhexanoate in n-butanol is added and the potassium salt of 7α-methoxy-3-methyl-8-oxo-7β-[D-2-phenyl-2-(thioformamido)acetamido]-5-thia-1-azabicyclo[4.2.-0]oct-2-ene-2-carboxylic acid is precipitated with ether.

EXAMPLE 2

7α-Methoxy-3-methyl-8-oxo-7β-[D-2-phenyl-2-(thioacetamido)acetamido]-5-thia-1-azabicyclo[4.2.-0]oct-2-ene-2-carboxylic acid 7β-(D-2-amino-2-phenylacetamido)-7α-methoxy-3-methyl-8-oxo-5-thia-1-azabicyclo[4.2.o]oct-2-ene-2-carboxylic acid is reacted with [(1-thioxoethyl)thio]acetic acid (prepared as described in U.S. Pat. No. 3,341,518) in the presence of triethylamine according to the procedure of Example 1 to obtain 7α-methoxy-3-methyl-8-oxo-7β-[D-2-phenyl-2-(thioacetamido)acetamido]-5-thia-1-azabicyclo[4.2.-0]oct-2-ene-2-carboxylic acid.

EXAMPLE 3

7α-Methoxy-7β-[D-2-(2-thienyl)-2-(thioformamido)acetamido]-3-(hydroxymethyl)-8-oxo-5-thia-1-azabicyclo[4.2.0]oct-2-ene-2-carboxylic acid-3-acetate a. D-α-[[[(4-methoxyphenyl)methoxy]carbonyl]amino]-2-thiopheneacetic acid 15.7 g. of D-α-(2-thienyl)glycine[m.p. 218°–219° (dec.) prepared from the racemate by means of D-camphor-10-sulfonic acid] nd 8 g. of magnesium oxide are suspended in 200 ml. of water. To this is added a solution of 22.8 g. of p-methoxybenzyloxycarbonyl azide in 200 ml. of dioxane and the mixture is stirred for 3 days at room temperature. The reaction mixture is filtered, the filtrate is extracted once with ether, the aqueous phase is layered over with ethyl acetate, cooled to about 10° and acidified to pH 2 with dilute hydrochloric acid. The aqueous phase is once more extracted with ethyl acetate, the combined extracts are washed once with water, dried with magnesium sulfate, filtered and concentrated. The residue is crystallized by triturating with petroleum ether. The crude D-α-[[[(4-methoxyphenyl)methoxy]carbonyl]amino]-2-thiopheneacetic acid is recrystallized from ethyl acetate/petroleum ether, yield, 25.2 g., m.p. 65°–67°.

b. 7-[D-2-(carboxy amino)-2-(2-thienyl)acetamido]-3-(hydroxymethyl)-7β-methoxy-8-oxo-5-thia-1-azabicyclo[4.2.0]oct-2-ene-2-carboxylic acid-3-acetate, N-(p-methoxybenzyl)ester 3.2 g. (0.01 mol.) of the product of part a are brought into solution in 40 ml. of methylene chloride with 1.1 mol. of N-methylmorpholine. This is cooled to −15°, 1.39 ml. of isobutylchloroformate are added and stirred for 10 minutes. To this mixture is added a solution of 4.8 g. (0.012 mol.) of 7-amino-7α-methoxycephalosporanic acid diphenylmethyl ester and 3.3 ml. of triethylamine in 40 ml. of methylene chloride. The reaction mixture is stirred for 1 hour at −5° and 1 hour at +5°. It is then evaporated to dryness in a rotary evaporator. The solid residue is triturated with ether and filtered under suction. The substance is dissolved in ice water, layered over with ethyl acetate and acidified to pH 2. The layers are separated, the aqueous layer is extracted once more with ethyl acetate, the combined extracts are washed with water, dried with magnesium sulfate and concentrated. The residue is dissolved in 200 ml. of ethyl acetate and the solution is treated with activated carbon. After filtering, the solution is slowly concentrated, whereupon the potassium salt of 7β-[D-2-(carboxymino)-2-(2-thienyl)acetamido]-3-(hydroxymethyl)-7α-methoxy-8-oxo-5-thia-1-azabicyclo[4.2.0]oct-2-ene-2-carboxylic acid-3-acetate, N-(p-methoxybenzyl) ester crystallizes.

c. 7β-[D-2-amino-2-(2-thienyl)acetamido]-3-(hydroxymethyl)-7α-methoxy-8-oxo-5-thia-1-azabicyclo[4.2.0]oct-2-ene-2-carboxylic acid-3-acetate 2g. of the product of part b are added to a mixture of 10 ml. of trifluoroacetic acid and 4 ml. of anisole at −5°. This is stirred for 10 minutes. It is then concentrated in a rotary evaporator, ether is added to the residue and it is filtered under suction. The crude 7β-[D-2-amino-2-(2-thienyl)acetamido]-3-(hydroxymethyl)-7α-methoxy-8-oxo-5-thia-1-azabicyclo[4.2.0]oct-2-ene-2-carboxylic acid-3-acetate, trifluoroacetic acid salt is added to 50 ml. of water and the solution is treated with 20 ml. of a solution of the acetate form of ion exchanger Amberlite LA-1 in isobutylmethyl ketone. The mixture is stirred for two hours at room temperature. The layers are separated, the aqueous phase is washed several times with ether and freeze dried. 7β-[D-2-amino-2-(thienyl)acetamido]-3-(hydroxymethyl)-7α-methoxy-8-oxo-5-thia-1-azabicyclo[4.2.0]oct-2-ene-2-carboxylic acid-3-acetate is obtained, which is treated with a little ethanol and filtered under suction.

d. 7α-methoxy-[D-2-(2-thienyl)-2-(thioformamido)acetamido]-3-(hydroxymethyl)-8-oxo-5-thia-1-azabicyclo[4.2.0]oct-2-ene-2-carboxylic acid-3-acetate 0.005 mol. of the product of part (C) is suspended in 35 ml. of ethylthioformate, cooled to 0°–5° and 0.01 mol. of a 10% solution of triethylamine in methylene chloride is added. After 15 minutes, a stream of hydrogen sulfide is passed in over a period of 15 minutes while stirring. The reaction mixture is stirred for an additional 3 hours at 0°–5°, petroleum ether is then added until precipitation is complete. The mixture is then filtered. The triethylamine salt of 7α-methoxy-7β-[D-2-(2-thienyl)-2-(thioformamido)acetamido]-3-(hydroxymethyl)-8-oxo-5-thia-1-azabicyclo[4.2.0]oct-2-ene-2-carboxylic acid-3-acetate thus obtained is dissolved in water, the solution is adjusted to pH 6.5 with sodium bicarbonate, filtered and the filtrate is acidified to pH 1.5 with 2N hydrochloric acid to obtain 7α-methoxy-[D-2-(2-thienyl)-2-(thioformamido)acetamido]-3-(hydroxymethyl)-8-oxo-5-thia-1-azabicyclo[4.2.0]oct-2-ene-2-carboxylic acid-3-acetate.

EXAMPLE 4

α-[(Thioxomethyl)amino]benzeneacetic acid, diphenylmethyl ester

A solution of 15.9 g. (0.05 mol.) of α-phenylglycine, diphenylmethyl ester, and 9 g. of (0.1 mol.) of ethylthioformate in 50 ml. of tetrahydrofuran is stirred overnight at room temperature. Then a stream of hydrogen sulfide is passed into the solution for 10 minutes, the reaction mixture is permitted to stand overnight, then concentrated and petroleum ether is added to the residue. 16.9 g. of α-[(thioxomethyl)amino]benzeneacetic acid, diphenylmethyl ester, crystallizes. The crude product is recrystallized from methanol, m.p. 129°–130°.

EXAMPLE 5

α-[(Thioxomethyl)amino]benzeneacetic acid 3.61 g. (0.01 mol.) of α-[(thioxomethyl)amino]benzeneacetic acid, diphenylmethyl ester, are added to a mixture of 30 ml. of trifluoroacetic acid and 5 ml. of anisole at 0°–5° and the mixture is stirred for 10 minutes. The mixture is concentrated, sodium bicarbonate solution is added to the residue and the aqueous phase is extracted with ether. This is then layered over with fresh ether, acidified and the aqueous phase is extracted twice with ether. Concentration of the ether solution yields α-[(thioxomethyl)amino]benzeneacetic acid as an oily residue.

EXAMPLE 6

7α-Methoxy-7β-[D-2-phenyl-2-(thioformamido)acetamido]-3-(hydroxymethyl)-8-oxo-5-thia-1-azabicyclo[4.2.0]oct-2-ene-2-carboxylic acid,diphenylmethyl ester To a solution of 0.01 mol. of 7-amino-7α-methoxy cephalosporanic acid, diphenylmethyl ester and 0.012 mol. of α-[(thioxomethyl)amino]benzeneacetic acid in 100 ml. of tetrahydrofuran is added at 0°–5° a solution of 0.011 mol. of dicyclohexylcarbodiimide in 20 ml. of tetrahydrofuran. The mixture is stirred for 90 minutes at room temperature, then filtered and concentrated. The residue is taken up in ethyl acetate, shaken with sodium bicarbonate solution and with water, dried with magnesium sulfate and again concentrated. Petroleum ether is added to the residue and 7α-methoxy-7β-[D-2-phenyl-2-(thioformamido)acetamido]-3-(hydroxymethyl)-8-oxo-5-thia-1-azabicyclo[4.2.0]oct-2-ene-2-carboxylic acid, diphenylmethyl ester, is obtained.

EXAMPLE 7

7α-Methoxy-7β[D-2-phenyl-2(thioformamido)acetamido]-3-(hydroxymethyl)8-oxo-5-thia-1-azabicyclo[4.2.0]oct-2-ene-2-carboxylic acid 2 g. of the product of Example 6 are added to a mixture of 20 ml. of trifluoroacetic acid and 1 ml. of anisole at 0°–5°, stirred for 10 minutes, concentrated and ether is added to the residue. 7α-methoxy-7β-[D-2-phenyl-2-(thioformamido)acetamido]-3-(hydroxymethyl)-8-oxo-5-thia-1-azabicyclo[4.2.0]oct-2-ene-2-carboxylic acid is obtained.

The following additional products having the formula in Column B of the following table are obtained according to the procedure of Example 2 by substituting for the [(1-thioxoethyl)thio]acetic acid the acid shown in Column A of the table and utilizing cephalosporins of Examples 2 or 3c or substituting for them the appropriately substituted cephalosporin of formula II above having the R, $R_1$ and X in the table:

TABLE I

| | A | | | B | |
|---|---|---|---|---|---|

$$R_2-\underset{S}{\overset{\|}{C}}-S-CH_2-COOH \quad R_1-\underset{\underset{\underset{R_2}{C=S}}{NH}}{CH}-CO-NH-\overset{OCH_3}{\underset{}{C}}-\overset{S}{\underset{}{CH}}\diagdown CH_2$$

(structure with $-C-N-$, $C-CH_2X$, $C-OR$, $=O$ groups forming the cephalosporin nucleus)

| Example | $R_2$ | R | $R_1$ | $R_2$ | X |
|---|---|---|---|---|---|
| 8 | $CH_3$ | $CH_3$ | H | $CH_3$ | H |
| 9 | $C_2H_5$ | H | $C_3H_7$ | $C_2H_5$ | $N_3$ |
| 10 | H | $-\underset{CH_3}{CH}O\overset{O}{\overset{\|}{C}}-CH(CH_3)_2$ | $C_6H_5CH_2-$ | H | $-OCOCH_3$ |
| 11 | $CH_3$ | $-\underset{CH_3}{CH}O\overset{O}{\overset{\|}{C}}-C_6H_5$ | $4-ClC_6H_4-$ | $CH_3$ | $-OCOCH_3$ |
| 12 | $C_2H_5$ | H | $4-OHC_6H_4-$ | $C_2H_5$ | H |
| 13 | $C_2H_5$ | H | $2-NH_2C_6H_4-$ | $C_2H_5$ | $-OCOCH_3$ |
| 14 | $CH_3$ | H | $C_6H_5$ | $CH_3$ | $N_3$ |
| 15 | H | $-CH_2O\overset{O}{\overset{\|}{C}}-CH_2C_6H_5$ | (thiophene) | H | $-OCOCH_3$ |
| 16 | H | H | H | H | H |
| 17 | $CH_3$ | H | (pyridine) | $CH_3$ | $-OCOCH_3$ |
| 18 | $C_2H_5$ | K | (furan) | $C_2H_5$ | $-OCOCH_3$ |
| 19 | $CH_3$ | $C_6H_5CH_2-$ | (phenyl) | $CH_3$ | $-OCOCH_3$ |
| 20 | $C_2H_5$ | $C_2H_5$ | (pyridine) | $C_2H_5$ | $-OCOCH_3$ |
| 21 | $CH_3$ | $C_2H_5$ | (thiophene) | $CH_3$ | $-OCOCH_3$ |
| 22 | H | $-CH_2O\overset{O}{\overset{\|}{C}}-CH(CH_3)_2$ | $4-(NHCONH_2)C_6H_4-$ | H | $N_3$ |
| 23 | $CH_3$ | H | $4-(CH_3SO_2NH)C_6H_4-$ | $CH_3$ | $-OCOCH_3$ |
| 24 | H | Na | $C_6H_5-$ | H | H |
| 25 | $CH_3$ | $CH_2O-\overset{O}{\overset{\|}{C}}-CH(CH_3)_2$ | $C_6H_5-$ | $CH_3$ | $-OCOCH_3$ |
| 26 | $CH_3$ | K | (thiane) | $CH_3$ | H |
| 27 | $C_3H_7$ | K | $C_6H_5-$ | $C_3H_7$ | $-OCOCH_3$ |
| 28 | $C_2H_5$ | H | (thiolane) | $C_2H_5$ | $-OCOCH_3$ |
| 29 | H | H | (cyclopentene) | H | $-OCOCH_3$ |
| 30 | $CH_3$ | H | (cyclohexyl) | $CH_3$ | H |

EXAMPLE 31

A sterile powder for reconstitution for use intramuscularly is prepared from the following ingredients which supply 1000 vials each containing 250 mg. of active ingredient:

7α-Methoxy-3-methyl-8-oxo-7-[D-2-phenyl-2-(thioformamido)acetamido]-5-

-continued

| | |
|---|---|
| thia-1-azabicyclo[4.2.0]oct-2-ene-2-carboxylic acid, potassium salt | 250 gm. |
| Lecithin powder, sterile | 50 gm. |
| Sodium carboxymethylcellulose, sterile | 20 gm. |

The sterile powders are aseptically blended and filled into sterile vials and sealed. The addition of 1 ml. of water for injection to the vial provides a suspension for intramuscular injection.

What is claimed is:

1. A compound of the formula

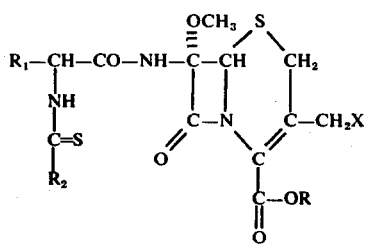

wherein R is hydrogen, lower alkyl, phenyl, tri(halo)-lower alkyl, phenyl-lower alkyl, aluminum, alkali metal, alkaline earth metal, lower alkylamine or

$R_1$ is phenyl, substituted phenyl wherein the phenyl substituent is lower alkyl, halogen, hydroxy, amino, ureido or methylsulfonylamino, furyl, thienyl or pyridyl; $R_2$ and $R_4$ each is hydrogen or lower alkyl; $R_3$ is lower alkyl, phenyl or phenyl-lower alkyl; and X is hydrogen, lower alkanoyloxy or azido.

2. A compound as in claim 1 wherein R is hydrogen, lower alkyl or alkali metal; $R_1$ is phenyl or thienyl; $R_2$ is hydrogen or lower alkyl; and X is hydrogen or acetoxy.

3. A compound as in claim 1 wherein $R_1$ is phenyl.

4. A compound as in claim 1 wherein $R_1$ is thienyl.

5. A compound as in claim 1 wherein R is hydrogen, lower alkyl or alkali metal; $R_1$ is hydrogen, phenyl or thienyl; $R_2$ is hydrogen or lower alkyl, and X is hydrogen or acetoxy.

6. A compound as in claim 3 wherein R, $R_2$ and X each is hydrogen.

7. Alkali metal salt of the compound of claim 6.

8. A compound as in claim 3 wherein R and X each is hydrogen, and $R_2$ is lower alkyl.

9. A compound as in claim 8 wherein the lower alkyl group is methyl.

10. A compound as in claim 4 wherein R and $R_2$ each is hydrogen, $R_1$ is 2-thienyl and X is acetoxy.

11. A compound as in claim 3 wherein R and $R_2$ each is hydrogen and X is acetoxy.

* * * * *